(12) United States Patent
Kim

(10) Patent No.: US 6,576,792 B2
(45) Date of Patent: Jun. 10, 2003

(54) 2-HALO-1-CYCLOALKENECARBOXAMIDES AND THEIR PREPARATION

(75) Inventor: Chang-Kyu Kim, Pittsford, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/849,474

(22) Filed: May 4, 2001

(65) Prior Publication Data
US 2002/0165413 A1 Nov. 7, 2002

(51) Int. Cl.⁷ ...................... C07C 233/58; C07C 231/02
(52) U.S. Cl. ..................... 564/191; 564/134; 564/189; 564/190
(58) Field of Search ................ 564/189, 190, 564/191, 134

(56) References Cited

U.S. PATENT DOCUMENTS

| | | |
|---|---|---|
| 4,708,959 A | 11/1987 | Shroot et al. |
| 4,851,541 A | 7/1989 | Maignan et al. |
| 5,082,966 A | 1/1992 | Moffatt |
| 5,118,690 A | 6/1992 | Minchin et al. |
| 5,210,088 A | 5/1993 | Minchin et al. |
| 5,315,009 A | 5/1994 | Austin et al. |
| 5,336,777 A | 8/1994 | Moffatt et al. |
| 5,373,016 A | 12/1994 | Brown et al. |
| 5,466,814 A | 11/1995 | Moffatt et al. |

FOREIGN PATENT DOCUMENTS

| | | | |
|---|---|---|---|
| DE | 2126865 | * | 11/1972 |
| DE | 4204492 | * | 2/1992 |

OTHER PUBLICATIONS

Baker et al, J. Org. Chem., vol 44, No. 6, pp 1022–1024, 1979.*
Viehe et al, Angew. Chem., No. 16, pp 616–617, 1971.*
Willi Ziegenbein/Wolfram Lang, "Eine neue Darstellung von–2–Chlor–cycloalken–(1)–carbonsauren–(1) und deren Hydrolyse zu a. w–Dicarbonsauren"; Aug. 1960; pp. 2743–2749.
Joachim Goerdeler/Werner Mittler, "Synthese von 3–Hydroxy–, 3–Alkoxy–und 3–Amino–isothiazolen"; Sep. 1962; pp. 944–948.

* cited by examiner

Primary Examiner—Shailendra Kumar
(74) Attorney, Agent, or Firm—Sarah Meeks Roberts

(57) ABSTRACT

The invention relates to a 2-halo-1-cycloalkenecarboxamides represented by Formula I:

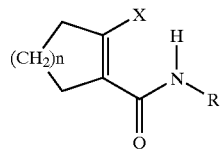

wherein
n is 1 or 2;
R is hydrogen or an alkyl group; and
X is a halogen.

26 Claims, No Drawings

2-HALO-1-CYCLOALKENECARBOXAMIDES AND THEIR PREPARATION

FIELD OF THE INVENTION

This invention relates to new chemical compounds belonging to the class of 2-halo-1-cycloalkenecarboxamides. It further relates to the preparation and the use of the compounds as intermediates in the production of a class of compounds useful as industrial biocides.

BACKGROUND OF THE INVENTION 4,5-Tri- and tetramethylene-4-isothiazolin-3-ones are a class of compounds known to have useful antimicrobial activity and several compounds of this type are commercially available and are used as industrial biocides. The preparation and use of such biocides have been described in the prior art, for example, in U.S. Pat. Nos. 4,708,959; 4,851,541; 5,082,966; 5,315,009; 5,336,777; and 5,466,814.

All of the preparations that have been disclosed in the prior art use either a mercapto intermediate which requires the use of hydrogen sulfide as a raw material in the preparation of the intermediate, or a sulfoxide (or sulfphinyl) intermediate which requires the use of benzyl mercaptan as a raw material in the preparation of the intermediate. Hydrogen sulfide, a colorless gas, and benzyl mercaptan, a colorless to pale yellow liquid, both have an obnoxious odor and require special equipment and handling in order to meet a "no-leak" and "no-spill" condition. It is, therefore, desirable to develop a new intermediate that does not require such an odorous gas or liquid raw material.

SUMMARY OF THE INVENTION

This invention provides novel 2-halo-1-cycloalkenecarboxamides represented by general Formula I:

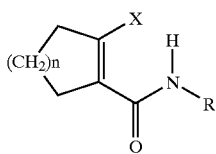

Formula I wherein
n is 1 or 2;
R is hydrogen or a substituted or unsubstituted alkyl group; and
X is a halogen.

In another aspect this invention provides a method of making a 2-halo-1-cycloalkenecarboxamide compound represented by Formula I, the method comprising:
(a) reacting a 2-oxo-1-cycloakylcarboxyester represented by Formula II;

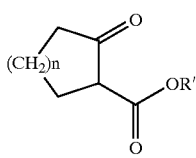

Formula II wherein
n is 1, or 2;

R' is methyl, or ethyl; with a halogenating agent to produce a mixture of 2-halo-1-cycloalkenecarboxyacid halide and 2-halo-1-cycloalkenecarboxyester, and
(b) subsequently reacting the mixture with ammonia or an alkylamine having the formula;

R—NH$_2$ wherein R is a substituted or unsubstituted alkyl group as defined for the R of the Formula I.

ADVANTAGEOUS EFFECT OF THE INVENTION

The present invention provides 2-halo-1-cycloalkenecarboxamides as intermediates for the preparation of 4,5-tri- and tetramethylene-4-isothiazolin-3-one biocides. Such intermediates can be converted to biocide precursors using an odorless solid raw material such as an ammonium or alkali-metal salt of hydrosulfide or thiocyanate. This provides for a safer and more efficient manufacturing process as it avoids spillage and gas leakage. There is also a reduced need for odor control.

DETAILED DESCRIPTION OF THE INVENTION

The compounds of the present invention are 2-halo-1-cycloalkenecarboxamides represented by Formula I;

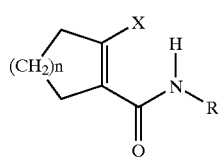

Formula I

In the above formula R can be any substituent that does not adversely affect the biocide activity or unduly interfere with the manufacture of the 4,5-tri- or tetramethylene-4-isothiazoline-3-one compounds. Preferably, R is hydrogen, or a substituted or unsubstituted alkyl group, such as an alkyl group containing 1 to 16, and more typically 1 to 12 carbon atoms. The alkyl group may be cyclic or branched. Examples of suitable alkyl groups include methyl, ethyl, propyl, butyl, pentyl, hexyl, octyl groups etc. Representative substituted alkyl groups include arylalkyl groups, heteroarylalkyl groups, or alkyl groups substituted with halogens, alkoxy or alkoxycarbonyl groups. Examples of suitable branched alkyl groups are isopropyl, 2-methylpropyl, sec-butyl, 3-methylbutyl, 3-methyl-2-butyl, 4-methyl-3-buten-2-yl, 2-pentyl, 3-pentyl, 2-hexyl and 3-hexyl groups. Examples of suitable cyclic alkyl groups are cyclopropyl, cyclobutyl, cyclopentyl, cyclohexyl and 4-methylcyclohexy groups. Examples of suitable arylalkyl groups are alkyl groups substituted with benzyl, 4-chlorobenzyl, 4-bromobenzyl, 4-nitrobenzyl, 4-ethoxycarbonylbenzyl, 4-methoxycarbonyl-benzyl and 4-cyanobenzyl groups. Examples of suitable heteroarylalkyl groups are 2-furylmethyl, 2-pyrrolemethyl, 2-pyridylmethyl, and 2-thienylmethyl groups. Examples of suitable alkyl groups substituted with halogens, alkoxy or alkoxycarbonyl groups are 2-chloroethyl, 2-bromoethyl, 3-chloropropyl, 4-chlorobutyl, methoxymethyl, 2-methoxyethyl, 2-ethoxyethyl, methoxycarbonylmethyl, ethoxycarbonylmethyl, 2-methoxycarbonylethyl and 2-ethoxycarbonylethyl groups.

n is 1 or 2. X is a halogen such as fluorine, chlorine, bromine, or iodine. Preferred halogens are chlorine and bromine.

When reference in this application is made to a particular group, unless otherwise specifically stated, the group may itself be unsubstituted or substituted with one or more substituents (up to the maximum possible number). For example, "alkyl" group refers to a substituted or unsubstituted alkyl group, while "benzene" refers to a substituted or unsubstituted benzene (with up to six substituents). The substituent may be itself substituted or unsubstituted. The particular substituents used may be selected by those skilled in the art to attain the desired biocidal properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided.

Generally, unless otherwise specifically stated, substituents include any substituents, whether substituted or unsubstituted, which do not destroy properties necessary for the biocidal utility. Examples of substituents include known substituents, such as: halogen, for example, chloro, fluoro, bromo, iodo; alkoxy, particularly those "lower alkyl" (that is, with 1 to 6 carbon atoms, for example, methoxy, ethoxy; substituted or unsubstituted alkyl, particularly lower alkyl (for example, methyl, trifluoromethyl); thioalkyl (for example, methylthio or ethylthio), particularly either of those with 1 to 6 carbon atoms; substituted and unsubstituted aryl, particularly those having from 6 to 20 carbon atoms (for example, phenyl); and substituted or unsubstituted heteroaryl, particularly those having a 5- or 6-membered ring containing 1 to 3 heteroatoms selected from N, O, or S (for example, pyridyl, thienyl, furyl, pyrrolyl); acid or acid salt groups such as any of those described below; and others known in the art. Alkyl substituents may specifically include "lower alkyl" (that is, having 1–6 carbon atoms), for example, methyl, ethyl, and the like. Further, with regard to any alkyl group or alkylene group, it will be understood that these can be branched or unbranched and include ring structures.

In another aspect the invention relates to a method of making the 2-halo-1-cycloalkenecarboxamide intermediates from 2-oxo-1-cycloalkylcarboxyesters (Formula II). Such cycloalkylcarboxyesters are readily available either by carboxylation and esterification of cycloalkylketone such as cyclopentanone or cyclohexanone, or self-condensation of dibasic esters such as dimethyl adipate or diethyl adipate.

The method of making the intermediates comprises a two-step non-isolation process as shown in the Scheme I below. The first step is reacting a 2-oxo-1-cycloakylcarboxyester represented by Formula II with a halogenating to produce a mixture of 2-halo-1-cycloalkenecarboxyacid halide and 2-halo-1-cycloalkenecarboxyester. The second step is subsequently reacting the mixture with ammonia or an alkylamine (R—NH₂) as defined below.

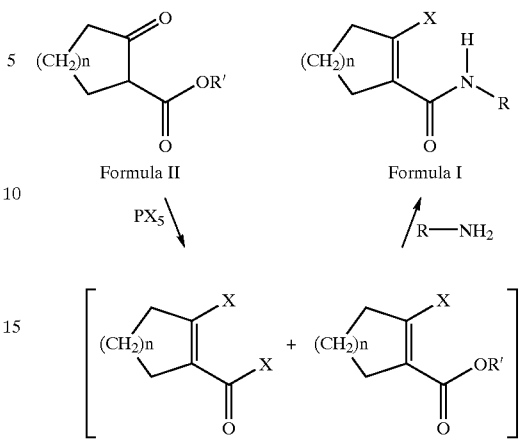

Scheme I wherein
n is 1 or 2;
R' is methyl or ethyl;
X is a halogen;
R is hydrogen or an alkyl group as defined above.

The first step reaction requires an excess amount of a strong halogenating agent in order to produce a mixture of 2-oxo-1-cycloalkylcarboxyacid halide and 2-oxo-1-cycloalkenecarboxy esters. A 2-halo-1-cycloalkenecarboxyacid halide is highly reactive and readily reacts with any alkylamine to form the desired intermediate, but a 2-halo-1-cycloalkenecarboxy-ester is not reactive and does not react at all with a higher alkylamine. It is, therefore, desirable to produce a large percentage of the carboxyacid halide. A preferred excess amount of the halogenating agent is in the range of 150–250 mole %. Useful halogenating agents are known to those skilled in the art. Preferred halogenating agents for the first step are phosphorus pentahalides (PX5) such as phosphorus pentachloride (PCl5) or phosphorus pentabromide (PBr5), and phosphorus trihalides (PX3) such as phosphorus trichloride (PCl3) or phosphorus tribromide (PBr3). A high reaction temperature is preferred for the first step reaction to maximize the ratio of carboxyacid halide to carboxyester. A preferred reaction temperature is in the range of 50–150° C. Suitable solvents for the first step reaction are aprotic organic solvents, for example, hexane, heptane, octane, nonane, petroleum ether, benzene, toluene, xylene, diethyl ether, di-isopropyl ether, tetrahydrofuran, ethyl acetate, propyl acetate, butyl acetate, and the like. Among them, hydrocarbon solvents, such as petroleum ether, hexane, heptane, octane, or nonane, are the most preferred solvents.

The second step reaction requires a base as an acid acceptor. Preferred bases are organic bases, for example, pyridine, triethylarnine, or N,N-dimethylaniline; or weak inorganic bases, for example, sodium bicarbonate, sodium carbonate, potassium bicarbonate, potassium carbonate, ammonium carbonate, ammonium acetate, or sodium acetate. Ammonia itself is a base, and an excess of ammonia may be used as a reagent and a base when R is hydrogen. An alkylamine is also a base, and an excess of it may be used as a base as well. Preferred solvents for the second step reaction are also aprotic organic solvents as in the first step reaction. Protic solvents may be used if the reverse order addition is viable. In such a case, a mixture of carboxyacid halide and carboxyester, the product of the first step reaction, either neat or in an aprotic solvent, is added to a mixture of an alkylamine and a base in a protic solvent. Examples of suitable protic solvents are water, methyl alcohol, ethyl alcohol, propyl alcohol, isopropyl alcohol, n-butyl alcohol, sec-butyl alcohol, t-butyl alcohol, or acetic acid. Water is the most preferred solvent for ammonia and a lower alkylamine having from 1 to 6 carbon atoms. A low reaction temperature is preferred for the second step reaction especially when a protic solvent is used. A preferred reaction temperature for the second step is in the range of −15 to 50° C.

The preparation of 4,5-tri- and tetramethylene-4-isothiazolin-3-one biocides from the intermediates of the invention (Formula I) is straightforward as shown in the Scheme II below.

Scheme II

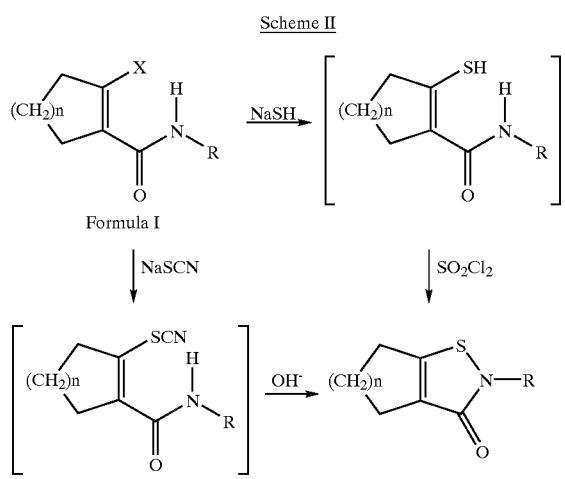

Formula I

R is as defined above. The sulfur functional group is introduced by replacing the halide in the intermediate with hydrosulfide or thiocyanate using an odorless solid raw material, sodium hydrosulfide, or sodium thiocyanate. Either a hydrosulfide or thiocyanate intermediate can be converted without isolation to the final biocide compound. Methods of converting such hydrosulfides or thiocyanates to 4,5-disubstitut-ed-4-isothiazolin-3-one type biocides is know to those skilled in the art and is well documented in the open literature.

The following examples illustrate the practice of this invention. They are not intended to be exhaustive of all possible variations of the invention. Parts and percentages are by weight unless otherwise indicated.

EXAMPLES

In the following are given two examples (Example 1 and Example 2) of the synthesis of the 2-halo-1-cycloalkenecarboxamide intermediates and an example (Example 3) of the preparation of a biocide from the inventive intermediates.

Example 1

2-Chloro-1-cyclopentenecarboxamide (n=1, R═H, and X═Cl)

In a 1-1 three-necked RB flask, place 125 g (0.6 m) of phosphorus pentachloride and 360 ml of heptane. Stir and heat slurry to 60° C. Add 57 g (0.4 m) of methyl 2-oxo-1-cyclopentanecarboxylate dropwise from a dropping funnel under nitrogen atmosphere at 60–65° C. over 2 hours. After the addition is complete, stir the reaction mixture at 65° C. for 1.5 hour. Distill heptane and phosphorus oxychloride under a reduced pressure at 55–60° C. (pot-temperature). Add 90 ml of fresh heptane and distill again to remove a residual phosphorus oxychloride. Transfer the resulting brown oil to a dropping funnel.

In a 500-ml three-necked RB flask, place 132 ml (2.0 m) of 59% ammonium hydroxide (ammonia in water) and cool to 0–5° C. in an ice-water bath. Add slowly the brown oil in the dropping funnel keeping the pot-temperature under 15° C. over 30 minutes. After the addition is complete, stir the reaction mixture at room temperature for an hour. Add 100 ml of toluene and stir at room temperature for another 20 minutes. Collect product, wash with water and toluene, and dry in an air oven. Yield: 31.9 g (55%) of gray solid.

Example 2

2-Chloro-1-cyclopentene-1-N-methylcarboxamide (n=1, R═CH₃, and X═Cl)

In a 1-1 three-necked RB flask, place 125 g (0.6m) of phosphorus pentachloride and 360 ml of heptane. Stir and heat slurry to 75° C. Add 57 g (0.4 m) of methyl 2-oxo-1-cyclopentanecarboxylate dropwise from a dropping funnel under nitrogen atmosphere at 80–85° C. over 2–3 hours. After the addition is complete, stir the reaction mixture at 85° C. for 5–10 minutes. Distill heptane and phosphorus oxychloride under an adjusted aspirator vacuum pressure at the pot-temperature of 55–60° C. Add 90 ml of fresh heptane and distill again to remove a residual phosphorus oxychloride. Transfer the resulting brown oil to a dropping funnel.

In a 500-ml of three-necked RB flask, place 155 g (2.0 m) of 40% methylamine in water, cool to 0–5° C. in an ice-water bath. Add slowly the brown oil in the dropping funnel keeping the pot-temperature under 15° C. over 30 minutes. After the addition is complete, stir the reaction mixture at room temperature for 2–3 hours. Add 200 ml of toluene, stir for 15 minutes, and separate toluene layer. Extract the water solution two times with 200 ml of toluene each. Combine toluene solution, dry over magnesium sulfate, treat with decolorizing carbon, filter and wash with toluene. Concentrate toluene solution to an oil under a reduced pressure. Cover the resulting oil with 200 ml of heptane and stir vigorously to crystallize product. Stir the slurry and cool to 0–5° C. in ice-water bath. Collect product, wash with heptane, and dry in an air oven. Yield: 32 g (50%) of off-white fluffy solid.

Example 3

2-Methyl-4,5-trimethylene-4-isothiazolin-3-one

In a 250-ml three-necked RB flask, place 16 g (0.1 m) of 2-chloro-1-cyclopentene-1-N-methylcarboxamide (see Example 2), 32 g (0.34 m at 60%) of sodium hydrosulfide hydrate, and 100 ml of isopropyl alcohol. Heat slowly the mixture with medium high speed stirring under gentle reflux (78–82° C.) for 4 hours. Keep under nitrogen atmosphere throughout the reaction. Separate isopropyl alcohol solution from dark brown gum, and rinse the gum remained in the flask twice with 50 ml of fresh isopropyl alcohol each. Combine isopropyl alcohol solution and concentrate under a reduced pressure. Dissolve the resulting dark brown residue in 100 ml of water, cool to 5–10° C., and acidify by adding slowly 20 ml of concentrated hydrochloric acid. Extract water solution trice with 100 ml of ethyl acetate each. Combine ethyl acetate solution, treat with decolorizing carbon, and concentrate under a reduced pressure to give yellow to orange oil.

Dissolve the oil in 50 ml of dichloromethane and 50 ml of formic acid and cool to 15° C. in a cold-water bath. Add 15.4 g (0.11 m) of sulfuryl chloride dropwise keeping the temperature at 20–25° C. Stir the reaction mixture at room temperature for 15 minutes. Distill methylene chloride and formic acid under a reduced pressure keeping the temperature at lower than 35° C. Dissolve the residue in 100 ml of water, cool in an ice-water bath while neutralizing to pH 7 with 50% caustic. Extract product three times with 100 ml of ethyl acetate each. Combine ethyl acetate solution, treat with decolorizing carbon, and concentrate under a reduced pressure till product starts to crystallize. Cool the slurry to −10° C. in an ice-acetone bath and stir at that temperature for an hour. Collect product, wash with chilled ethyl acetate, and dry in an air oven. Yield: 8.7 g (56%) of off-white crystalline solid.

The invention has been described in detail with particular reference to certain preferred embodiments thereof, but it will be understood that variations and modifications can be effected within the spirit and scope of the invention.

What is claimed is:

1. A 2-halo-1-cycloalkenecarboxamide compound represented by Formula I:

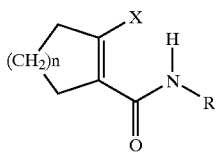

wherein
  n is 1 or 2;
  R is a substituted or unsubstituted alkyl group; and
  X is a halogen.

2. The compound of claim 1 wherein R is a substituted or unsubstituted alkyl group containing less than 12 carbon atoms.

3. The compound of claim 1 wherein R is a substituted or unsubstituted alkyl group containing less than 6 carbon atoms.

4. The compound of claim 1 wherein X is chlorine or bromine.

5. The compound of claim 2 wherein X is chlorine or bromine.

6. A method of making a compound represented by Formula I comprising:
  (a) reacting a 2-oxo-1-cycloakylcarboxyester represented by Formula II;

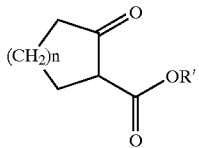

wherein
  n is 1 or 2;
  R' is methyl or ethyl; with a halogenating agent to produce a mixture of 2-halo-1-cycloalkenecarboxyacid halide and 2-halo-1-cycloalkenecarboxyester, and
  (b) subsequently reacting the mixture with ammonia or an alkylamine having the formula;

wherein R is a substituted or unsubstituted alkyl group.

7. The method of claim 6 wherein the halogenating agent is phosphorus pentahalide or phosphorus trihalide.

8. The method of claim 6 wherein the halogenating agent is used in excess.

9. The method of claim 8 wherein the halogenating agent is used in the range of 150–250% excess.

10. The method of claim 6 wherein step (a) is performed at a temperature in the range of 50–150° C.

11. The method of claim 6 wherein step (a) is performed in an aprotic solvent.

12. The method of claim 11 wherein the aprotic solvent is a hydrocarbon solvent.

13. The method of claim 6 wherein step (b) is performed in the presence of a base.

14. The method of claim 13 wherein the base comprises pyridine, triethylamine, or N,N-dimethylaniline, sodium bicarbonate, sodium carbonate, potassium bicarbonate, potassium carbonate, ammonium carbonate, ammonium acetate, or sodium acetate.

15. The method of claim 13 wherein the base is an excess of the ammonia, or alkylamine.

16. The method of claim 6 wherein step (b) is performed in an aprotic or protic solvent.

17. The method of claim 16 wherein the protic solvent is water.

18. The method of claim 6 wherein step (b) is performed at a temperature in the range of −15 to 50° C.

19. The method of claim 6 wherein R is an alkyl group having less than 12 carbon atoms.

20. A method of making a compound represented by Formula I comprising:
  (a) reacting a 2-oxo-1-cycloakylcarboxyester represented by Formula II;

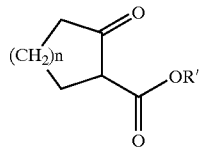

wherein
  n is 1 or 2;
  R' is methyl or ethyl; with an excess of a halogenating agent at a temperature in the range of 50–150° C. in an aprotic solvent to produce a mixture of 2-halo-1-cycloalkenecarboxyacid halide and 2-halo-1-cycloalkenecarboxyester, and
  (b) subsequently reacting the mixture in the presence of a base with ammonia or an alkylamine having the formula;

wherein R is a substituted or unsubstituted alkyl group.

21. The method of claim 20 wherein the halogenating agent is phosphorus pentahalide or phosphorus trihalide.

22. The method of claim 20 wherein the aprotic solvent is a hydrocarbon solvent.

23. The method of claim 20 wherein the base is an excess of the ammonia, or alkylamine.

24. The method of claim 20 wherein step (b) is performed using water as the solvent.

25. The method of claim 20 wherein step (b) is performed at a temperature in the range of −15 to 50° C.

26. The method of claim 20 wherein R is an alkyl group having less than 12 carbon atoms.

* * * * *